(12) United States Patent
Berdia (10) Patent No.: US 10,555,765 B2
(45) Date of Patent: Feb. 11, 2020

(54) SMALL JOINT FUSION PLATE AND CUTTING BLOCK

(71) Applicant: Sunjay Berdia, McLean, VA (US)

(72) Inventor: Sunjay Berdia, McLean, VA (US)

( * ) Notice: Subject to any disclaimer, the term of this patent is extended or adjusted under 35 U.S.C. 154(b) by 147 days.

(21) Appl. No.: 15/654,682

(22) Filed: Jul. 19, 2017

(65) Prior Publication Data
US 2018/0021073 A1      Jan. 25, 2018

Related U.S. Application Data

(60) Provisional application No. 62/364,288, filed on Jul. 19, 2016.

(51) Int. Cl.
*A61B 17/80* (2006.01)
*A61B 17/17* (2006.01)
*A61B 17/15* (2006.01)

(52) U.S. Cl.
CPC .......... *A61B 17/8061* (2013.01); *A61B 17/15* (2013.01); *A61B 17/17* (2013.01)

(58) Field of Classification Search
CPC ...... A61B 17/80; A61B 17/8061; A61B 17/15
See application file for complete search history.

(56) References Cited

U.S. PATENT DOCUMENTS

2010/0130981 A1*   5/2010   Richards ............... A61B 17/15
                                                              606/87
2012/0078376 A1*   3/2012   Vanasse ............... A61F 2/4261
                                                              623/21.12

* cited by examiner

*Primary Examiner* — Christopher J Beccia
(74) *Attorney, Agent, or Firm* — Attentive Law; Paul Ratcliffe (57) ABSTRACT

A method and one or more devices for a capitolunate fusion includes a cutting block for attaching to the capitate bone and for cutting the capitate and lunate bones to fit a corresponding plate. The cutting block is removed and a fusion plate is fixed to the capitate and lunate bone with the plate having a capitate section and a lunate section with the capitate section and lunate section of the plate in a generally perpendicular arrangement to allow optimal fusion of the capitate and lunate bones. Further devices include a three and four bone fusion cutting block and fusion plate.

6 Claims, 11 Drawing Sheets

PRIOR ART

SMALL JOINT FUSION PLATE AND CUTTING BLOCK

RELATED APPLICATION

This application claims priority to U.S. Provisional Patent Application 62/364,288 filed on Jul. 19, 2016, entitled "SMALL JOINT FUSION PLATE AND CUTTING BLOCK", the entirety of both are incorporated herein.

FIELD OF THE INVENTION

The present invention related to a method and devices for a surgical implant for aligning bones for fusion. Specifically, the present invention is ideally suited for aligning and fusing wrist bones through use of a surgical bone cutting block and corresponding bone plate.

BACKGROUND

Figure 1:
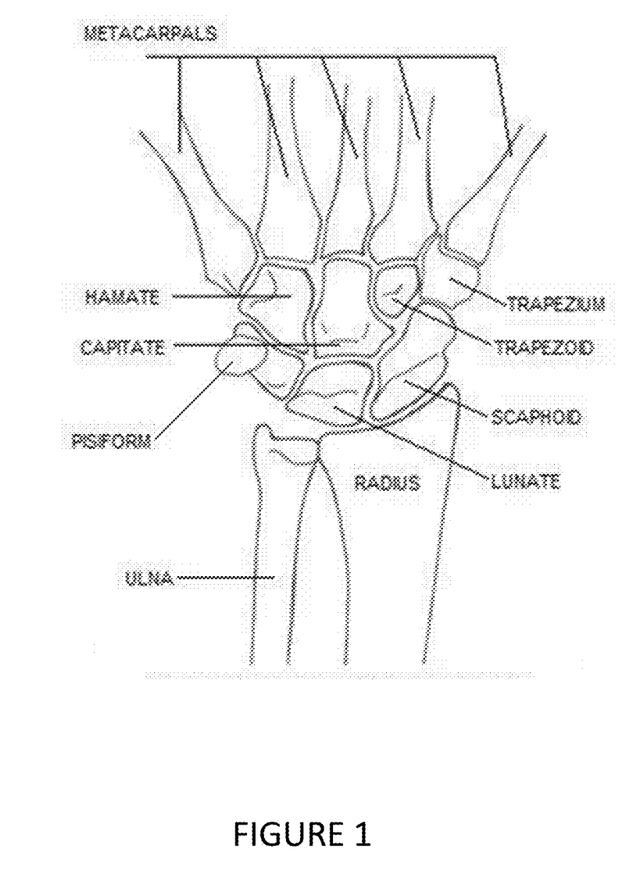
FIG. 1 is a detail view of the bones of the hand and wrist for explanatory purposes.

Arthritis, a common problem with many people, is a wearing or loss of the cartilage at any joint. The wearing or thinning cartilage can lead to inflammation, pain, loss of motion, and deformity. Arthritis can affect any joint including the wrist joint which contains numerous bones called carpal bones (as seen in FIG. 1). Fusing joint is a common orthopaedic surgical solution used to address arthritis and joint instability. In the wrist, there are two common forms of arthritis named specifically scaphoid nonunion advanced collapse (SNAC) and scaphoid lunate advanced collapse (SLAC). These types of arthritis result in a predictable progression of arthritis that involves the carpal bones of the wrist. One surgical procedure to address the arthritis is to perform a scaphoid excision and limited intercarpal fusion. Currently the most common form of intercarpal fusion involves fusion of the lunate-capitate-hamate-triquetral carpal bones. This is also referred to as the four-corner fusion. The four corner fusion fuses together the four carpal bones by various fusion or fixation methods or techniques. These fixation techniques include K-wires, headless screws, circular plates, and memory staples.

The problem with K-wires is they are unable to provide compression across the fusion plane, have limited fixation strength, are less rigid, and can lead to pin tract infections which can often result in early removal. Compression across a fusion plane is beneficial as it increases fusion rate and time to fusion. In addition, they often lead to secondary surgical procedures to remove the K-wires if they were buried during the index procedure.

Headless screws are technically challenging to use, usually provide less optimal compression across the fusion plane, and can lead to ulnar cutaneous nerve injuries. Further, when using a capitolunate headless screw one must choose the antegrade or retrograde position. In order to the insert the screw antegrade, one has to penetrate and create a hold in healthy viable cartilage of the lunate bone. Furthermore, the retrograde option is technically difficult, suboptimal in terms of screw purchase into the lunate, and the compression across the fusion plane is not perpendicular.

Figure 2A:
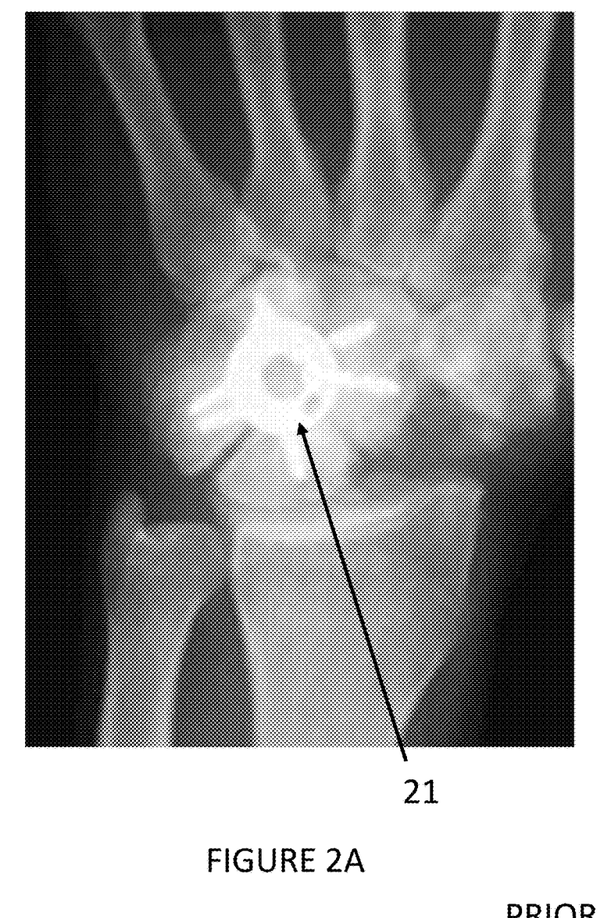
FIG. 2A is an image of a wrist with a circular 4 corner plate fixed to the wrist bones.

As seen in FIG. 2A, circular plates 21 have been used to assist in the four-corner fusion. The problem with the rather large circular plates 21 include: (1) nonunion or loose hardware; (2) hardware impingement; (3) post-operative pain; (4) low patient satisfaction; (5) limited pain-free patients; and (6) the plate alignment and installation procedure are technically difficult to achieve consistent success. The two most significant of these complications is the nonunion rate and hardware impingement. Reasons for the nonunion include the fact that these circular plates have limited ability to compress across the fusion planes. Further, although the current circular plate systems are designed to create a depression on the dorsal carpal bones through a reaming process, the plate must still partially rest on the dorsal lunate. This part of the dorsal lunate normally articulates with the dorsal distal radius at the upper ranges of wrist extension. Thus, these plates are prone to inherently impinge against the dorsal radius causing pain, decreased pain satisfaction, and at times necessitating plate removal.

Figure 2B:
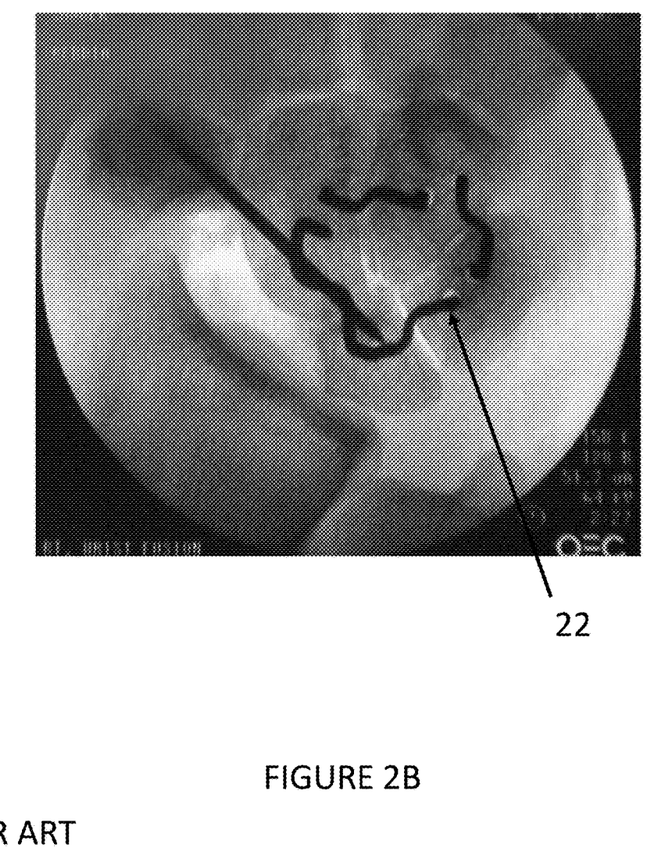
FIG. 2B is an image of a wrist with a 4 corner fusion using staples.

As seen in FIG. 2B, memory stapes 22 provide an alternative to the circular plates or K-wires. Staples are also known to have inherent problems. Staples 22 can be difficult to insert and immediately start compressing when they touch the bone or when they are released from the inserting tool. Some staples require a secondary heating process to compress the staples which can cause bone necrosis and decrease fusion rates. Further, the tines on the staples do not provide a rigid fixation like screws, the staples can back out of the bone and they are not as strong as titanium (yield strength of 690 Mpa vs. 1000 Mpa for screws).

When attempting to fuse two bones, forcing compression of the bones against each other is a critical factor that determines if the bones will fuse or not. Ideally, one wants the compression force to be as perpendicular to the bone surfaces being fused. An additional problem with staples is that compression across the fusion is non-linear as the compression is greater at the end of the staples and less at the bridge. The force vector of the compression is therefore not perpendicular to the fusion In addition to four corner fusions for wrist arthritis, two other forms of intercarpal fusion options exist. Three bone fusions consist of fusing the lunate, capitate, and hamate. Two bone fusion consists of fusing the lunate and capitate. With these two options, the triquetrum can either be removed or left in place but just not part of the fusion. In order to perform these two types of fusions, current techniques use similar constructs of K-wires, headless screws, or staples as described above for four corner fusions. There are no specific circular plates designed for two or three bone fusions.

In all three fusion options (2, 3, or 4 bone), the lunate needs to be fused with the capitate. The problem with performing a capitolunate fusion with screws is that the bones are very co-linear and there is not a good way to insert a screw across the fusion plane. Further, since ideal fusion stems from compression perpendicular to the fusion plane, access to and alignment of the perpendicular axis of the fusion plane is a significant challenge. When using a plate construct to fuse the lunate to the capitate, prominent dorsal hardware on the lunate presents a concern and the technique is difficult to reproduce.

Screw fixation of capitolunate can provide greater linear compression and more rigid fixation than stapes. However, inserting these screws can be a technical challenge for surgeons into these two carpal bones due to their size, shape and location. Two current techniques in inserting these screws freehand include: (1) antegrade; and (2) retrograde. Both techniques are difficult to perform, not ideal in angle or purchase of the bone, and not easily reproducible.

Figure 3A:
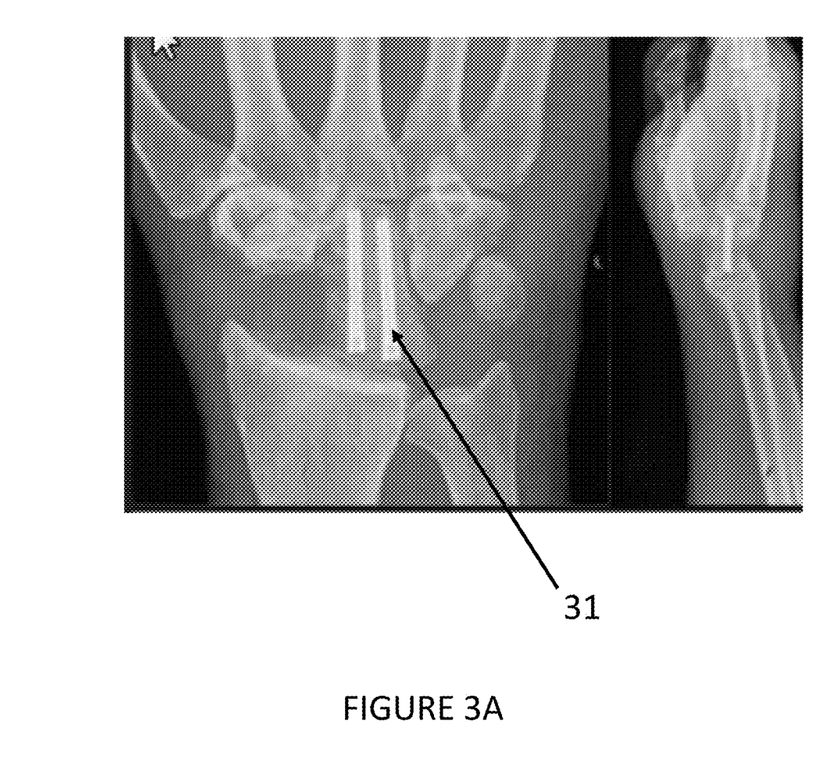
FIG. 3A is an image of a wrist after a capitolunate fusion using screws in an antegrade fashion.
Figure 3B:
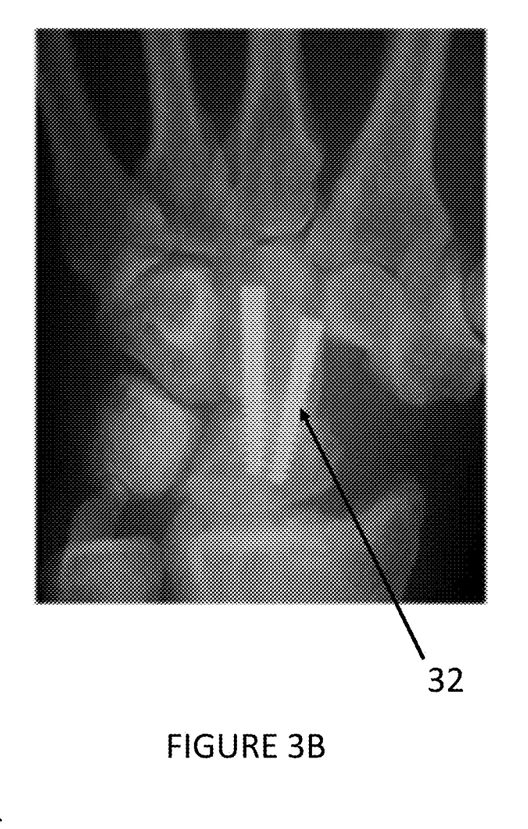
FIG. 3B is an image of a wrist after a capitolunate fusion using screws in a retrograde fashion.
Figure 4A:
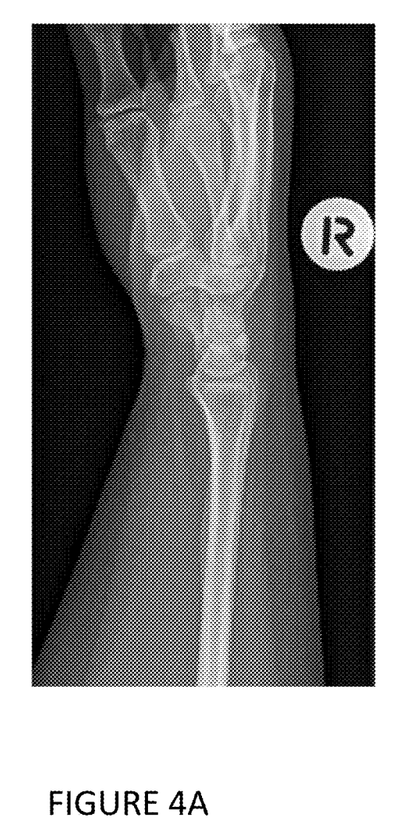
FIG. 4A is a radiographic image showing a profile view of perspective view of a human wrist.
Figure 4B:
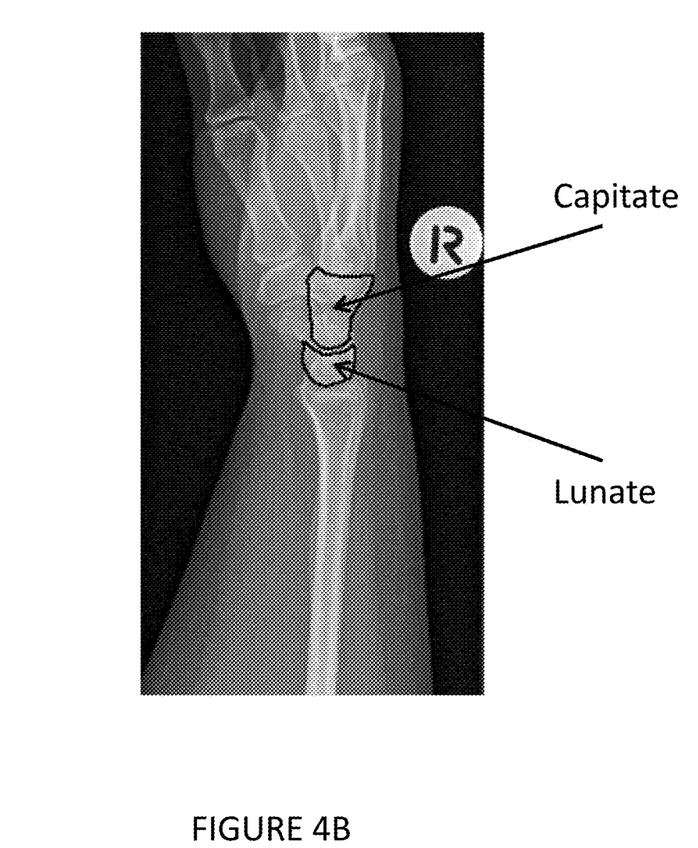
FIG. 4B is the same radiographic image with the capitate and lunate outlined in black.

Unfortunately, screws are also not an optimal solution as a stand-alone device or method for capitolunate fusions. As seen in FIGS. 3A and 3B, the screw or screws 31, 32 are inserted into the main part of the capitate and lunate bones to provide optimal fusion. However, as seen in FIG. 4, the alignment 41 of the capitate and lunate bones relative to each other is difficult to obtain an optimal insertion procedure. In the antegrade method (see FIG. 3A), screw 31 insertion requires significant release to allow hyperflexion of the wrist. The procedure also leaves holes in good lunate cartilage. Sometimes, proximal screw prominence from migration or settling can be a problem causing damage to distal radius cartilage damage and requiring a second surgery to remove the screw. In the retrograde method (see FIG. 3B), the dorsal capitate technique is used which is technically difficult for surgeons to perform as the screw 32 insertion is not perpendicular to the fusion plate, it does not provide optimal lunate purchase, requires an intercarpal technique, is more difficult than the antegrade procedure, can lead to neurovascular injury; and can cause damage to carpometacarpal joints.

When placing a screw antegrade from the lunate to the capitate, two challenges are encountered. First, in order to get a screw as perpendicular to a standard fusion plane which would be the best compression and rigid fixation, one needs to perform significant release of the wrist joint in order to achieve extreme wrist flexion. In many patients with wrist arthritis, they already have significant wrist contractures making achieving this wrist flexion even more difficult. Secondly, in order to get this perpendicular path across the fusion plane, one has to drill and make a hole in the lunate cartilage. Again, this is not ideal as after the procedure the "new" wrist joint will be wholly comprised on this radiolunate articulation.

Placing the screw in a retrograde fashion would avoid this last issue. However, because of the anatomic relationship of the lunate-capitate-third metacarpal, insertion of the screw is very difficult. These bones are co-linear and tightly bond. There is no edge or location that allows a screw to be inserted that is perpendicular to the fusion. Currently, surgeons utilizing this technique will usually place the screw(s) somewhat oblique to the fusion.

Therefore, what is needed is a new technique and device or devices enabling use of a screw to fuse the capitate and lunate bones which is generally perpendicular to the fusion plane. Ideally the device would not rest on the dorsal surface of the lunate so it wouldn't impinge on the distal radius. Variation of the device should allow for performing a 2, 3, or 4 bone fusion.

SUMMARY

Therefore, what is needed is a simplified method of capitolunate fusion which improves the fusion potential by providing consistent compression of the capitate and lunate bones along an axis generally perpendicular to the fusion plane. The present invention provides such solution by providing an improved method and device for isolated 2 bone fusion of the capitate and lunate by a capitate cutting block and a capitolunate plate. For 3 and 4 bone fusion, the block is extended to a capitate-hamate cutting block and two additional variations of the plate allow for additional screw purchase into the hamate (3 and 4 bone fusion) or into hamate and triquetrum (4 bone fusion).

The capitate cutting block is designed to aid the surgeon in reproducibly being able to remove the exact right amount of bone material from the capitate bone and lunate bone (if needed) to allow proper fitting and alignment of the capitolunate fusion plate. The present invention allows the screw or screws to be inserted in a near perpendicular alignment to the fusion plane of co-linear bones. The present invention makes use of a cutting block that allows one to remove a wedge of bone in the capitate bone in a precise reproducible manner. The wedge created not only accurately matches the fusion plate but allows screw(s) to placed so that there are more perpendicular to the fusion plane. A variation of the capitate cutting block may include a semi-circular metal extension that would allow for the block to more securely and reproducibly rest on the capitate. The extension would mirror the circular shape of the proximal aspect of the capitate.

The capitate-hamate cutting block is similar to the capitate-lunate cutting block but it extends ulnarly and aids in removing a wedge of the hamate as well. A variation of this block would also include a metal extension proximally that would mirror the circular shape of the proximal capitate and possibly the proximal hamate.

The capitolunate plate is ideally suited to fuse the capitate and lunate carpal bones. In the preferred method, two holes are designed to capture and insert from the capitate to the lunate. These holes are angled to allow the screws to be more perpendicular to the fusion. These holes allow for locking or non-locking screws. They can also be variably angled. The screws can be locking, non-locking, fully, or partially threaded. The preferred method is to use non-locking partially threaded screws placed in a slightly angled position by using an angled drill guide. The distal part of the plate sits on the dorsal wedge on the capitate and a set of holes for screws also. These holes are angled slightly distally and allow for locking or non-locking screws. They can also be variably angled. The screws can be locking, non-locking, fully, or partially threaded.

The capito-hamate-lunate plate is ideally suited to fuse the capitate, hamate, and lunate carpal bones. In the preferred method, one hole is designed to capture and insert from the capitate to the lunate and one hole is designed to capture and insert from the hamate to the lunate. These holes are angled to allow the screws to be more perpendicular to the fusion plane. These holes allow for locking or non-locking screws. They can also be variable angled. The screws can be locking, non-locking, fully, or partially threaded. The preferred method is to use non-locking partially threaded screws placed in the slightly angled position by using an angled drill guide. The distal part of the plate rests on the capitate and hamate. In the preferred method, there would be two set of variably angled locking holes that allow purchase into the capitate and hamate.

The capito-hamate-lunato-triquetrum plate is ideally suited to fuse the capitate, hamate, lunate, and triquetrum carpal bones. In the preferred method, two holes are designed to capture and insert from capitate to lunate and two holes are designed to capture and insert from the hamate and triquetrum. One variation of the plate would only have one hole from the capitate to the lunate. Another variation would only have one hold from the hamate to the triquetrum. The distal part of the plate would rest on the capitate and hamate. In the preferred method, there would be two set of variably angled locking holes that allow purchase into the capitate and hamate.

The present invention provides a fixation plate kit for bone fusions in a wrist. The kit includes a cutting block and a fixation plate. The cutting block has at least one hole for temporarily securing the cutting block to a capitate bone and a plurality of cutting slits for providing access to the capitate bone and other wrist bones for cutting into the bones. The cutting block has a first portion and a second portion where at least one opening is present in the first portion allowing the cutting to create a first surface or plane on the capitate bone. The cutting block second portion has a second slit or opening allowing the surgeon to cut the bone and create a second surface or plane on the capitate or additional and alternative bones in the wrist. The first surface and second surface are angled away from each other in a generally perpendicular direction, although the angle could be acute or obtuse.

The cutting block is configured to allow the surgeon to cut the bone away in the capitate and other appropriate bones to allow for the kit's fixation plate. The fixation plate comprises an elongated plate having a first end and a second end. The first end having a first surface with at least one hole for securing the fixation plate to the capitate bone; and the second end having a second surface extending from the first surface, at a transition point, and forming an angle with the first surface; wherein the second surface has at least one hole through the second end for securing the second end of the fixation plate to at least one additional bone. The fixation plate first surface is general perpendicular to the second surface although the angle could be acute or obtuse. The fixation plate is ideally a capitolunate plate. The plate can be configured for a two-bone fusion, three-bone fusion, or four-bone fusion.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

The present invention, as seen in FIGS. 5A-8B, provides various cutting blocks and bone fusion plates ideally suited for the wrist and wrist bones.

Figure 5A:
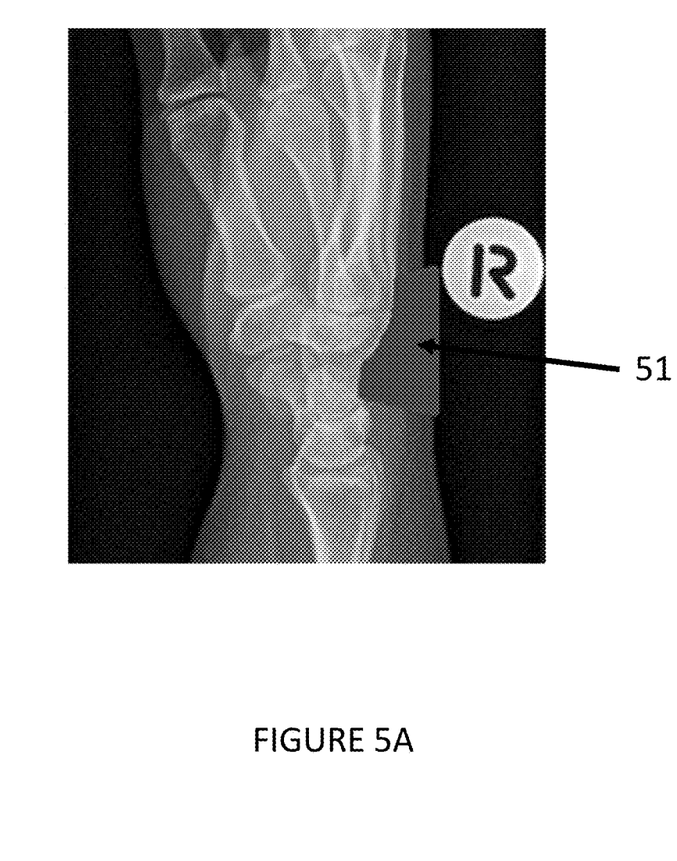
FIG. 5A is an x-ray image of a human wrist showing the cutting block of the present invention aligned along the capitate and lunate bones.
Figure 5B:
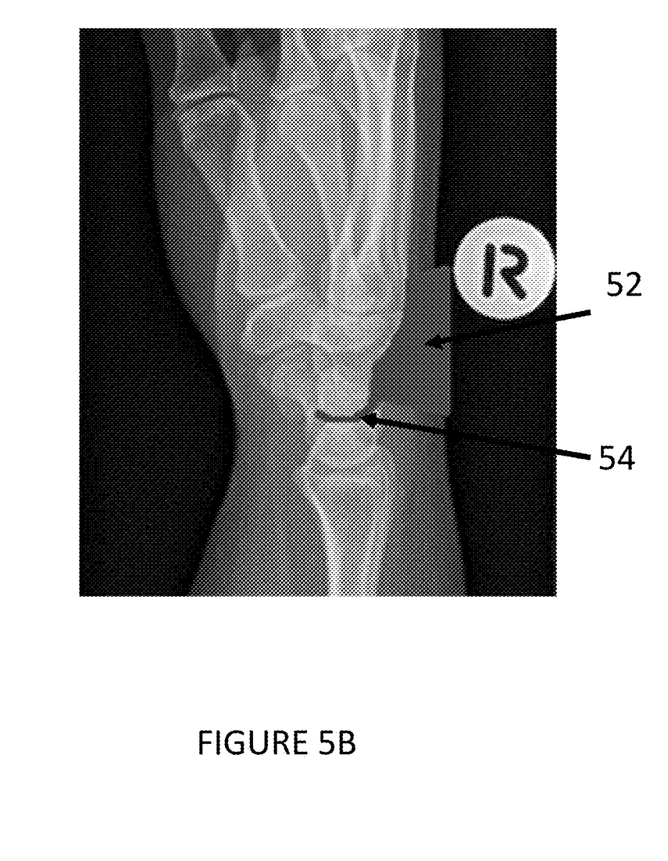
FIG. 5B is an example of variation of the cutting block with a curved extension that would rest under the proximal capitate.
Figure 5C:
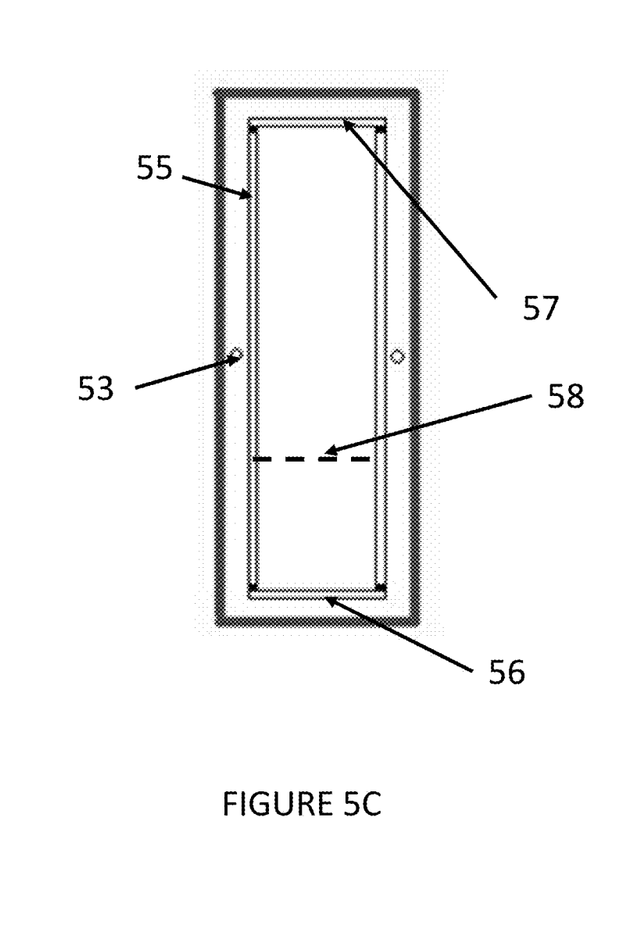
FIG. 5C is a top view of the cutting block of the present invention.

As seen in FIGS. 5A-5C, the present invention provides a cutting block 51, 52 designed to create a wedge cut (see FIG. 5D) into the capitate bone. The cutting block 51, 52 has a curvature or concave portion on the bottom surface or bone mating side (as seen in FIGS. 5A and 5B) configured to mate with the capitate bone or curved to mate with the curvature of the capitate bone. The curvature allows the cutting block 51,52 to securely rest on top of the capitate bone and holds the cutting block 51, 52 in place before it is secured (i.e. with K-wires). The cutting block 51, 52 may also be designed for the surgeon to cut a section of bone on the lunate bone. The cutting block 52 (FIG. 5B) is a variation of the cutting block 51 (FIG. 5A) where there is proximal curved extension 54 that allows the block 52 to tightly rest under the head of the capitate. The cutting block 52 with the curved extension 54 allows a more secure and reproducible fit of the cutting block 52 onto to the capitate.

The cutting block 51, 52 has one or more holes 53 for K-wires to secure the block to the capitate bone. The cutting block 51, 52 also has slits 55, 56, and 57 designed for receiving the saw blade (not shown) used to make the cuts into the capitate and possibly the lunate if needed. The superior part of the block 51, 52 compared to the inferior part may have varying heights allowing for varied depth of cut into the bone. Additional control of the depth is possible by etching the saw with a limiter line, or by welding a limiter block on the saw. In a preferred embodiment, the superior slit 57 is roughly 90 degrees out of the plane with the inferior slit 56. The design provides an end result with a wedge cut into the capitate in a general 90-degree angle allowing the plate to sit deep within the capitate so as to prevent dorsal impingement of the plate and the dorsal distal radius. The cutting block 51, 52 may also be designed to have fewer slits or more slits; or with a different mechanism such as a resting shelf to help guide the saw. The slits 55, 56, 57 are for use with the cutting saw and may be angled slits. There may be more than one slit 55 connecting or extending the superior slit 57 and inferior slit 56. Further, slit 55 may be a series of one or more slits or openings with varying depths or angles. In addition, the cutting block may be configured to work with standard square end cutting blades or angled blades, which might match the desired angle of the two surfaces created by the cuts from the inferior or superior slits 56, 57.

The cutting block 51, 52 may also incorporate one or more lines to mark when or where to stop cutting. The cutting block 51, 52 may be provided in different sizes such as small, medium, and large. Further, the cutting block 51, 52 is designed, so that once the bone material and cutting block are removed the opening from the cut fits the capitolunate plate (the "CL Plate") including the angle α of the CL Plate 61 (see FIG. 6C).

Figure 5D:
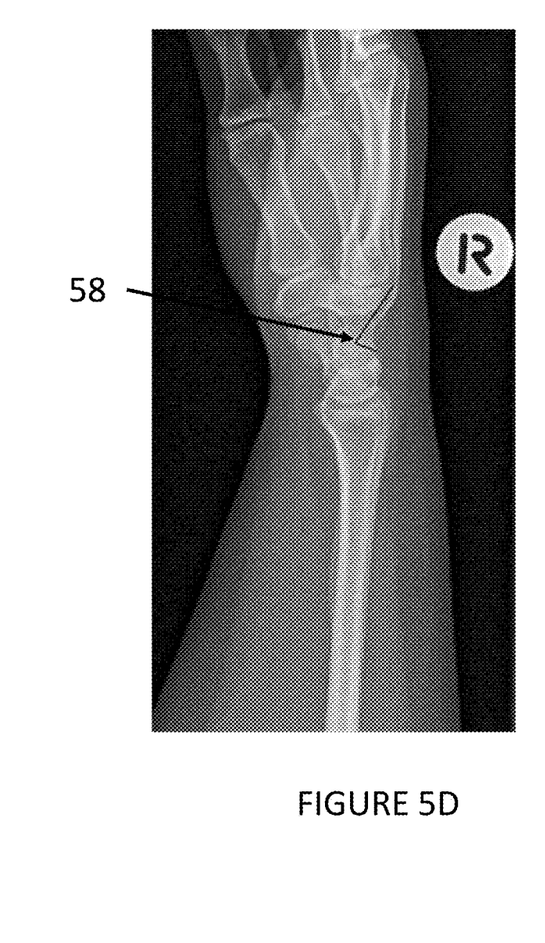
FIG. 5D is radiographic view of wedge cut that would be created after using the cutting block.
Figure 6A:
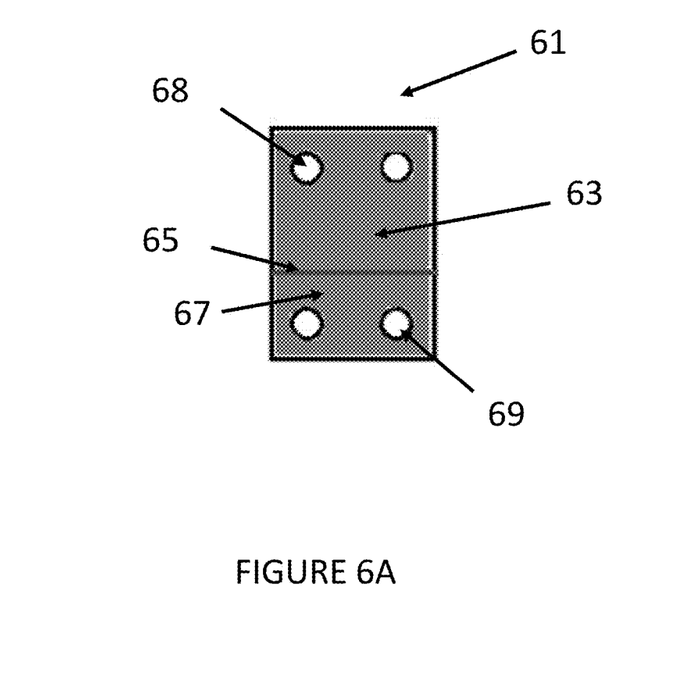
FIG. 6A is a top view of the capitolunate fusion plate of the present invention.
Figure 6B:
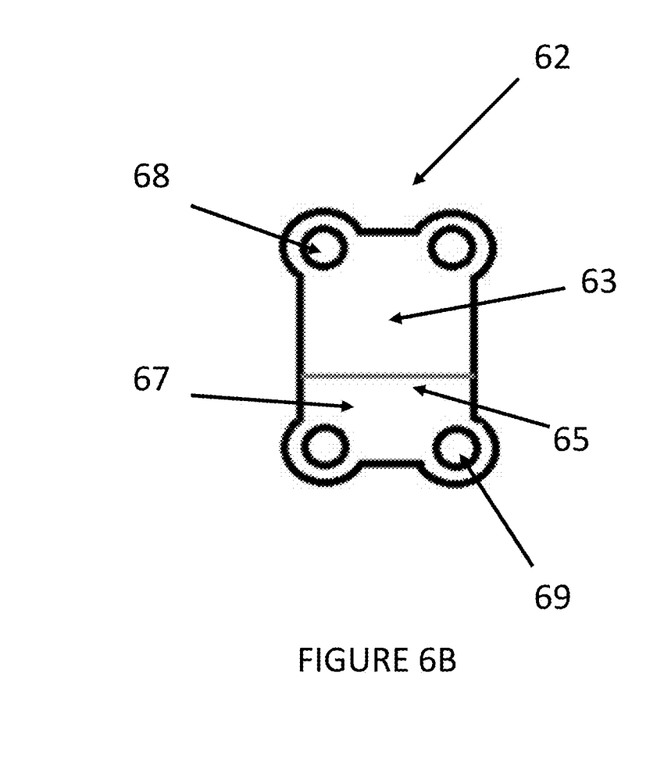
FIG. 6B is a top view of an additional embodiment of a capitolunate fusion plate of the present invention.

The cutting block 51, 52 is designed to create an opening FIG. 5D to fit a capitolunate (CL) Plate. The generic version of the CL Plate 61 is seen in FIG. 6A. An additional embodiment of the butterfly CL Plate 62, is seen in FIG. 6B which has rounded edges at the corners. The rounded edges could allow the plate 62 to sit deeper within the wedge cut, be less prominent dorsally, and cause less chance of dorsal impingement. Other versions of a CL Plate are also possible which may have less curvature at the edges or may be narrower at one end (ulnarly). In both versions, the CL Plate 61, 62 has an upper portion 63 which sits on the distal dorsal capitate bone and a lower portion 67 which rest in the wedge created in the proximal capitate. The CL Plate 61 has one or more upper holes 68 allowing the upper portion 63 of the CL Plate 61 to be fixed or attached to the capitate bone. The CL Plate 61, 62 has one or more lower holes 69 allowing the lower portion 67 of the CL Plate 61, 62 to be attached to the lunate bone but also partly go through the proximal part of the capitate. The upper portion 63 and lower portion 67 of the CL Plate 61, 62 are connected but set an angle α which is generally 90 degrees, see FIG. 6C. However, the angle α need not be 90 degrees.

Figure 6C:
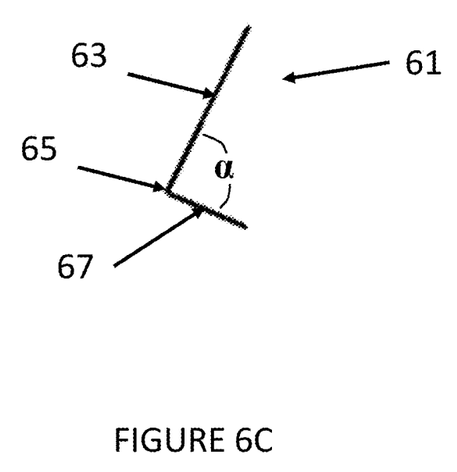
FIG. 6C is the side view of the capitolunate fusion plate of the present invention.

The CL Plate 61, 62 is angled so that the screw(s) that are placed across the fusion plane or joint are nearly perpendicular. Perpendicular compression is preferred as it is known to increase fusion rates and decrease the time to fusion. In order to achieve even a better angle to get perpendicular, the screws themselves can be variably angled so that they are not completely perpendicular to the plate. Variably angled screw fixation is a common technique used in orthopaedics.

In a preferred embodiment, the CL Plate would use two 2.3 mm screws to attach the upper portion 63 to the capitate bone and two 2.3 mm screws to attach the lower portion 67 to the lunate bone. The screws may be locking and may also be partially threaded with non-locking threaded lag screws. They can be fixed or variably angled.

As seen in FIGS. 6A and 6B, the CL Plate 61, 62 would be fixed to the wrist allowing the upper portion 63 to be fixed to the capitate bone and in conjunction with the lower portion 67 allows for screw fixation across the fusion plane. The plate 61, 62 transition point 65 from the upper portion 63 to the lower portion 67 and is also where the bend in the plate is with an angle α.

Figure 7:
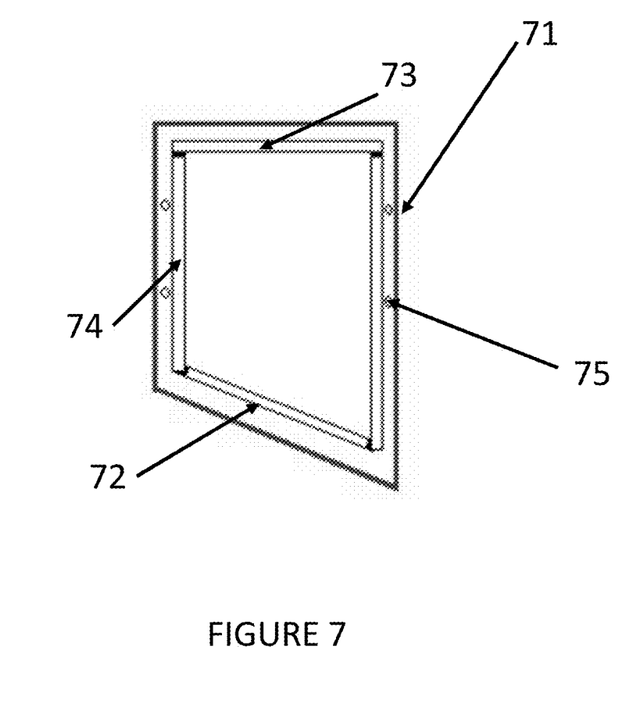
FIG. 7 is a top perspective view of an illustrative example of a multi-bone wrist cutting block in accordance with the present invention.
Figure 8A:
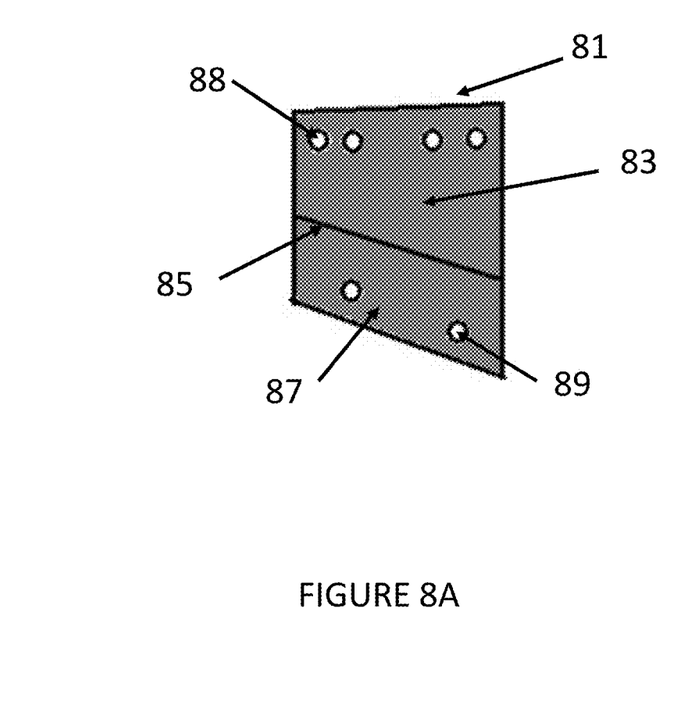
FIG. 8A is a top perspective view of one example of a generic three-bone carpal fusion plate in accordance with the present invention.
Figure 8B:
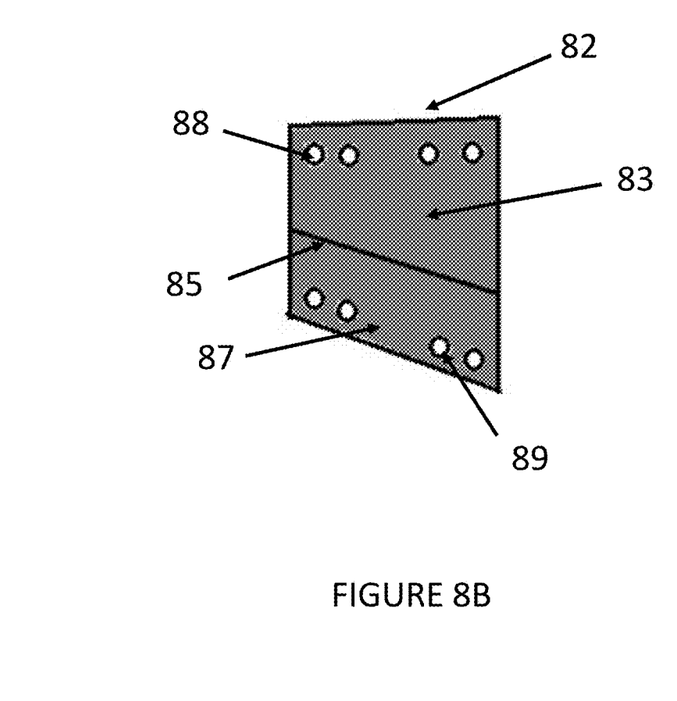
FIG. 8B is a top perspective view of one example of a generic four-bone carpal fusion plate in accordance with the present invention.

An alternative embodiment of the preferred invention is shown in FIGS. 7-8B, which displays a cutting block 71 (FIG. 7) and plates (FIGS. 8A-8B) for a three and four bone fusion. FIG. 7 shows a superior view of the cutting block 81 for a 3 or 4 bone fusion which is designed to create an opening to fit the plate 81, 82 as seen in FIGS. 8A and 8B. This block 71 makes a wedge cut within the capitate and hamate carpal bones. The block may also an inferior curve metal extension that would sit in the midcarpal space underneath the capitate and hamate articular surfaces allowing more resting stability. The 3-bone plate 81 (FIG. 8A) has an upper portion 83 for mating with the capitate bone and the hamate bone through use of the upper holes 88. The plate 81 has a lower portion 87 for mating with the lunate bone through use of the lower holes 89 and the use of screws as previously described. The 4-bone plate 82 (FIG. 8B) has an upper portion 83 for mating with the capitate bone and the hamate bone through use of the upper holes 88. The plate 82 has a lower portion 87 for mating with the lunate bone and the triquetrum bone through use of the lower holes 89 and the use of screws as previously described. Further embodiments of the Plate 81, 82 may include rounded corners, narrower proximally than distally, and/or curved edges.

The upper portion 83 and lower portion 87 of the plate 81, 82 are connected with a bend at 85 but set at an angle α which is generally 90 degrees. However, the angle α need not be 90 degrees. However, a generally perpendicular compression at the fusion plate is ideal. For the three bone plate 81, the lower portion 87 of the plate 81 is proximate to and designed so that the screws can be placed nearly perpendicular to the fusion plane between the capitate and lunate. For the four bone plate 82, the lower portion 87 of the plate 82 is proximate to and designed so that radial screws can be placed nearly perpendicular to the fusion plane between the capitate and lunate and ulnar screws can be placed nearly perpendicular to the fusion plane between the hamate and triquetrum. Because of the asymmetric nature of the capitate and hamate and the rest of the carpal bones, there may be a need for cuttings blocks and plates designated for the right and left sides when performing three and four bone fusions.

In use, the surgeon installs the cutting block 51 to the patient's capitate bone using K-wires. The surgeon then cuts the bone from the capitate bone (in a 2-bone fusion) to conform within the design of the cutting block 51 to provide a wedge cut into the capitate bone. The first and second plane in a generally perpendicular orientation to each other using slits 56 and 57. Next, the surgeon uses a saw through the two parallel slits 55 to complete the wedge resection. The surgeon then removes the K-wires and block from the capitate. Small osteotomes can then be used to help remove the wedge of bone from the capitate. The surgeon then reduces the capitate and lunate in the most appropriate position which is co-linear in most cases. K-wires can be used to temporarily hold this position. The surgeon then installs the fusion Plate 61, 62 and inserts one or more screws into the capitate bone through the top fusion plate hole(s) 68. Next, the Next the surgeon installs one or more screws into the lunate bone through the bottom fusion plate hole(s) 69 forming a generally perpendicular fixation and compression between the capitate and lunate bones allowing for maximum fusion success. Alternatively, the surgeon could install the plate 61,62 and place screw(s) into the lunate bone first and then the capitate bone.

Figure 9A:
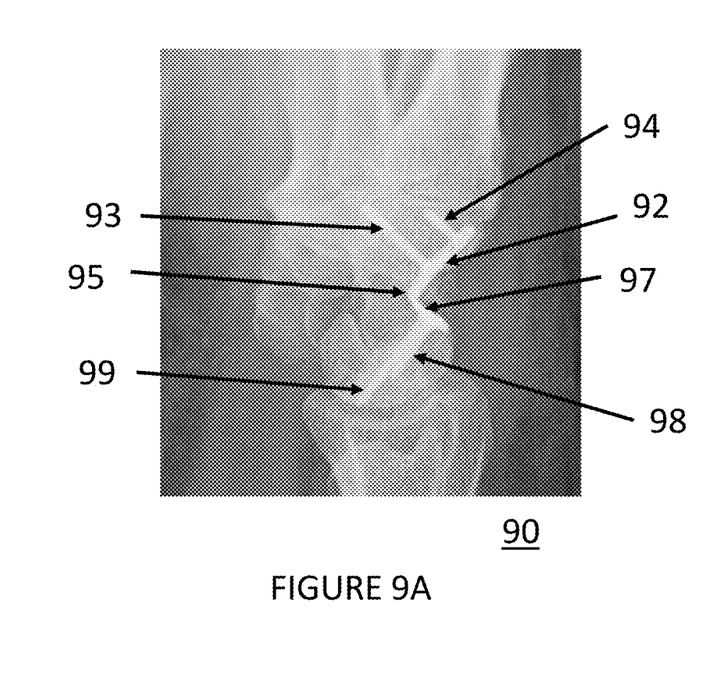
FIG. 9A is a side view of an additional embodiment of the fixation plate fixed to one or more bones in a wrist in accordance with the present invention.
Figure 9B:
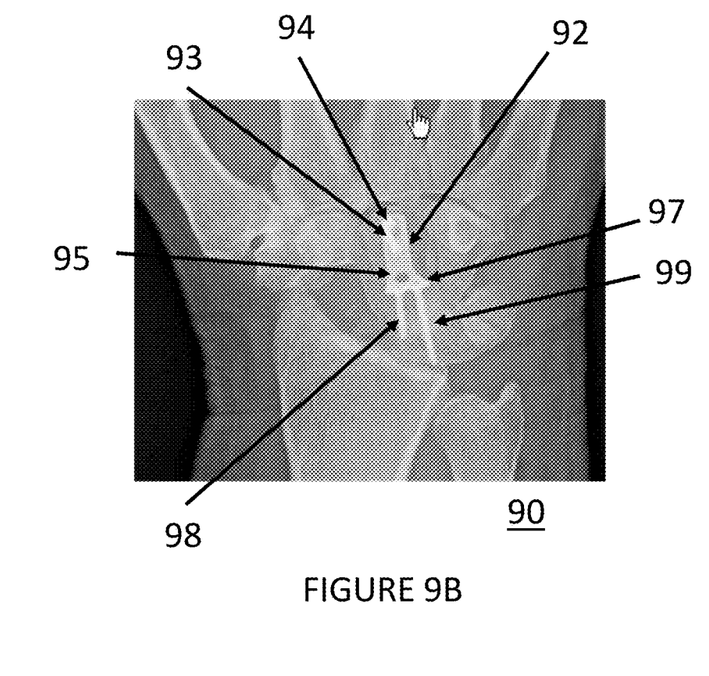
FIG. 9B is a top perspective view an additional embodiment of the fixation plate fixed to one or more bones in a wrist in accordance with the present invention.

An additional embodiment is depicted in FIGS. 9A and 9B which illustrate a side and top perspective view of a fixation plate fixed to one or more bones in a wrist. The fixation plate 90 mechanism includes the fixation plate having a first end 97 and a second end 92. The first end 97 is affixed to the capitate bone by two screws or other attachment devices and described herein 98, 99. The second end 92 is affixed to one or more other bones in the wrist by bone by two screws or other attachment devices and described herein 93, 94. In this embodiment, the first end has two openings which are perpendicular to the longitudinal direction of the fixation plate and are configured to receive the two screws 98, 99. The second end has two openings which run along the axis of the fixation plate and are configured to receive the other two screws 93, 94.

Further, the first end 97 has its top surface which is generally perpendicular to the top surface of the second end 92. The two surfaces meet or extend from the transition point 95. Through this fixation plate and generally perpendicular or angled two surface configuration, the bones in the wrist can be fixed to the plate and aligned allowing for improved or proper fusion.

It will be understood that various details of the present subject matter may be changed without departing from the scope of the subject matter. Furthermore, the foregoing description is for the purpose of illustration only, and not for the purpose of limitation.

I claim:

1. A fixation plate kit for bone fusions comprising:

a cutting block having a capitate bone mating surface, a cutting side, and at least one hole, and a plurality of slits, wherein the capitate bone mating surface having a concave portion configured to mate with a capitate bone, the cutting side having an opening configured to provide access for cutting, and the at least one hole is configured to secure the cutting block to the capitate bone and the plurality of slits are configured to provide access to the capitate bone and at least one additional wrist bone for cutting into the capitate bone or at least one additional wrist bone, wherein the cutting block has a first planar portion and a second planar portion;

wherein a first slit in the first planar portion is configured to provide access to create a first plane on the capitate bone;

wherein a second slit in the second planar portion is configured to provide access to create a second plane on at least one additional bone; and a fixation plate comprising an elongated plate having a first end and a second end;

the first end having a first surface with at least one hole through the first end configured to provide access to secure the fixation plate to the capitate bone; and the second end having a second surface extending from the first surface and forming an angle with the first surface; wherein the second surface has at least one hole through the second end configured for securing the second end of the fixation plate to at least one additional bone.

2. The fixation plate kit of claim 1, wherein the fixation plate first surface is generally perpendicular to the second surface.

3. The fixation plate kit of claim 1, wherein the fixation plate is a capitolunate plate.

4. The fixation plate kit of claim 1, wherein the fixation plate is configured for a three-bone fusion.

5. The fixation plate kit of claim 1, wherein the fixation plate is configured for a four-bone fusion.

6. The fixation plate kit of claim 1, wherein the cutting block has a curved extension protruding from a lower surface of one end of the block, wherein the curved extension is configured to receive a head of the capitate bone.

* * * * *